United States Patent [19]

Sucher

[11] Patent Number: 5,256,136
[45] Date of Patent: Oct. 26, 1993

[54] CARPAL TUNNEL APPLIANCE

[76] Inventor: Benjamin M. Sucher, 5261 E. Fanfol Dr., Paradise Valley, Ariz. 85253

[21] Appl. No.: 951,816

[22] Filed: Sep. 28, 1992

[51] Int. Cl.$^5$ ............................................. A61F 5/00
[52] U.S. Cl. ..................................... 602/21; 128/879; 273/67 B
[58] Field of Search ............... 602/5, 6, 21, 62–64; 128/879, 26; 2/16, 20, 158, 159, 161 A, 162; 273/54 B, 166, 67 B; 84/467–469; 482/44, 55

[56] References Cited

U.S. PATENT DOCUMENTS

| | | | |
|---|---|---|---|
| 1,558,666 | 10/1925 | Brewer et al. | 273/67 B |
| 1,797,057 | 3/1931 | Foulke | 602/21 |
| 3,203,006 | 8/1965 | Shirey | 2/159 |
| 3,526,006 | 9/1970 | Beardmore | 602/21 X |
| 3,581,740 | 6/1971 | Sherbourne | 602/21 X |
| 3,703,894 | 11/1972 | Galloway et al. | 602/21 |
| 3,818,905 | 6/1974 | Lebold | 602/21 |
| 4,516,774 | 5/1985 | Nankivell | 273/67 B |
| 4,558,694 | 12/1985 | Barber | 602/21 |
| 4,738,447 | 4/1988 | Brown | 2/161 A X |
| 4,807,606 | 2/1989 | Hasegawa et al. | 602/21 |
| 4,874,168 | 10/1989 | Wright | 273/67 BX |
| 4,913,418 | 4/1990 | Schlueter et al. | 482/55 |
| 5,031,640 | 7/1991 | Spitzer | 128/879 X |
| 5,102,120 | 4/1992 | Lindblad | 482/55 X |

Primary Examiner—Richard J. Apley
Assistant Examiner—Linda C. M. Dvorak
Attorney, Agent, or Firm—Cahill, Sutton & Thomas

[57] ABSTRACT

Compression of the median nerve is relieved or prevented with a glove having a contoured major surface for receiving a hand for treatment. A wall intersecting the major surface includes a first wall portion for positioning the index finger and a second wall portion for positioning the thumb. The first and second wall portions of the wall meet at a corner. The major surface increases in height along said first and second wall portions with increasing distance from the corner. The hand rests on the major surface with the wrist and fingers extended, and the thumb extended and abducted. This positioning spreads the palm and bends the fingers back, all of which stretches the transverse carpal ligament and enlarges the carpal canal, ultimately relieving pressure on the median nerve, alleviating or preventing symptoms of carpal tunnel syndrome.

13 Claims, 2 Drawing Sheets

CARPAL TUNNEL APPLIANCE

BACKGROUND OF THE INVENTION

This invention relates to the treatment or prevention of carpal tunnel syndrome and, in particular, to a glove-like appliance for opening the carpal canal by stretching and releasing the transverse carpal ligament and the surrounding structure of the hand, wrist, and forearm of a person.

"Carpal Tunnel Syndrome" is the result of a compromised or narrowed carpal canal leading to compression injury of the median nerve in the wrist. The carpal tunnel is the canal in the wrist through which the median nerve and flexor tendons pass from the forearm to the hand. Prolonged, repetitive motion at a keyboard is a common, but by no means the only, cause of the syndrome.

To date, carpal tunnel syndrome has been treated with orthotics, such as wrist splints or wrist rests, antiinflammatory medications, cortisone injections, or surgery. Alone or combined, these treatments have met with varying degrees of success. The obvious solution, removing the cause of the injury, is not always practical since, as in the case of using a keyboard, the cause of the injury is often the means by which the patient obtains his or her livelihood. The next best choice, prevention through proper preparation, can be achieved by enlarging the carpal canal to maintain adequate space for the median nerve and thus avoid compression.

It has been discovered that the carpal canal can be enlarged by osteopathic manipulation and stretching, thereby alleviating compression on the median nerve and resolving carpal tunnel syndrome. While severe cases may require other treatment, the manipulation is effective in the majority of cases and has the advantage of being prophylactic, i.e. a preventative.

While manipulation is effective, there are two difficulties. Optimum resolution of the symptoms requires frequent, vigorous stretching and the assistance of another person, the physician. Suitably instructed, a patient can enhance the treatment with stretching. Thus, there is a need for an appliance which a patient can use several times daily to augment treatment by the physician.

Simply prescribing the use of an appliance does not mean that the patient will use it properly, e.g. as often as prescribed. Proper use depends on the compliance or self-discipline of the patient. It also depends on how easy it is to use the appliance. In general, an appliance that is mechanically simple and is easy to use will more likely be used as directed.

Several terms are used herein relating to the movement of the fingers and thumb. The fingers and thumb bend or "flex" to grasp a broom handle. If a hand lies with the palm and fingers flat on a flat surface, the fingers are "extended" or straightened. Lifting the fingers, and not the palm, off the surface further extends the fingers. "Abducting" the thumb means moving the thumb away from the fingers while the thumb rests on the surface. "Extending" is lifting the thumb, and not the palm, off the surface. If the forearm also rests on the surface, "extending" the wrist means lifting the palm, and not the forearm, off the surface. These terms relate to the relative movements of the fingers, thumb, palm, and wrist to each other, not to the flat surface. The flat surface is used merely as an aid for visualizing the movements.

In view of the foregoing, it is therefore an object of the invention to provide a glove-like appliance for self-treatment or prevention of carpal tunnel syndrome.

Another object of the invention is to provide a mechanically simple, easily used appliance, thereby improving compliance, enhancing the effectiveness of the treatment, and increasing the likelihood of a successful outcome.

A further object of the invention is to provide a glove for relieving the pressure on the median nerve by stretching the transverse carpal ligament and stretching the flexor tendons into the carpal canal for dilitation effect.

SUMMARY OF THE INVENTION

The foregoing objects are achieved in the invention in which a glove-like appliance (herein referred to simply as a glove) includes a plate or disc having a contoured major surface for receiving the hand. The plate is divided into unequal quadrants aligned with the knuckles and the radial side of the index finger (the side facing the thumb). A wall extends from the edge of the plate toward the center, then curves back to the edge, forming a rounded corner having an angle of approximately ninety degrees and defining a first quadrant. A second quadrant, under the fingers, increases in thickness with distance from the knuckles to the fingertips. A third quadrant, diagonally opposite the second and receiving the thumb, increases in thickness with distance from the base to the tip of the thumb. A fourth quadrant, diagonally opposite the first, receives the palm of the hand and includes a recess near the edge of the plate, approximately centered under the heel of the hand. A strap extends across the plate and attaches to the edge of the plate for holding the hand in place.

The glove preferably rests on a horizontal surface about waist high, e.g. a desk, table, or counter. The hand is placed on the major surface with the index finger and thumb against the wall. The second quadrant extends the fingers and the third quadrant extends and abducts the thumb. With the elbow straight or slightly bent, the user leans into the glove, bending the wrist backward, stretching the flexor tendons and connected muscles. The pressure on the heel of the hand and the abduction of the thumb flatten the heel of the hand into the recess, stretching the transverse carpal ligament. The stretching is continued for several seconds and then the hand is relaxed. The process is repeated several times per session, several sessions per day.

BRIEF DESCRIPTION OF THE DRAWINGS

A more complete understanding of the invention can be obtained by considering the following detailed description in conjunction with the accompanying drawings in which.

DETAILED DESCRIPTION OF THE INVENTION

Figure 1:
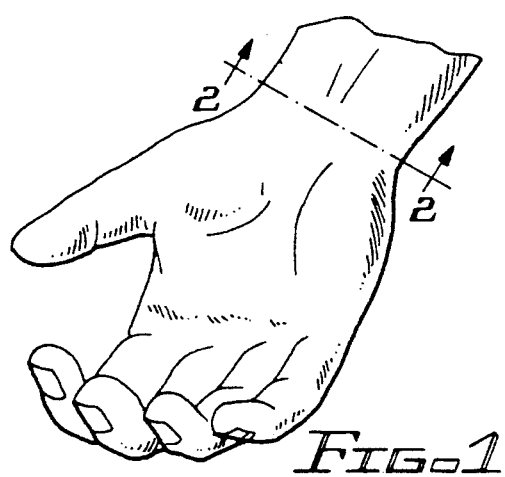
FIG. 1 illustrates the palmar side of a right hand in a relaxed position.
Figure 2:
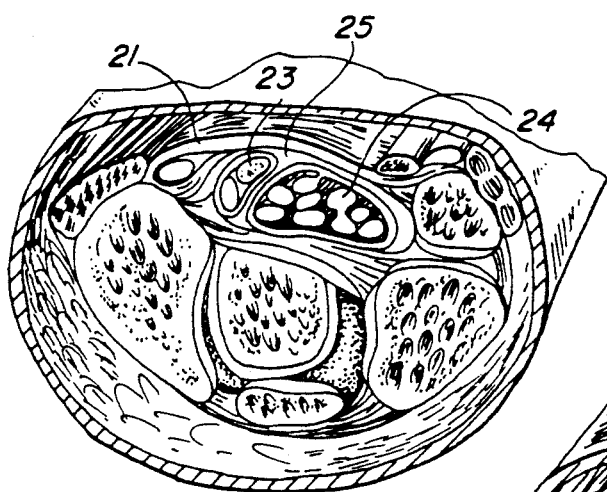
FIG. 2 illustrates a cross-section through the wrist of the hand illustrated in FIG. 1.

Referring to FIGS. 1 and 2, a human right hand in the relaxed position has the fingers flexed slightly, a hollow or concave palm, and the thumb flexed. In the wrist, illustrated in FIG. 2, transverse carpal ligament 21 spans the heel of the hand at the wrist and overlies the carpal canal containing median nerve 23 and flexor tendons 24.

Figure 3:
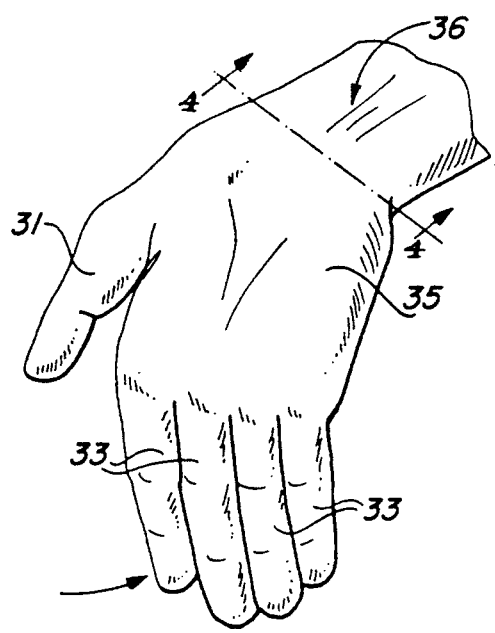
FIG. 3 illustrates a right hand with the thumb, fingers, and wrist extended to stretch the transverse carpal ligament and flexor tendons.

In accordance with one aspect of the invention, the compression of the median nerve can be relieved by extending the hand as illustrated in FIG. 3. Specifically, thumb 31 is extended and abducted away from the palm, flattening palm 35. Fingers 33 are bent backward relative to palm 35 and palm 35 is bent backward relative to forearm 36. Thus, the palm is spread open from side to side and from front to back, flattening the palm.

Figure 4:
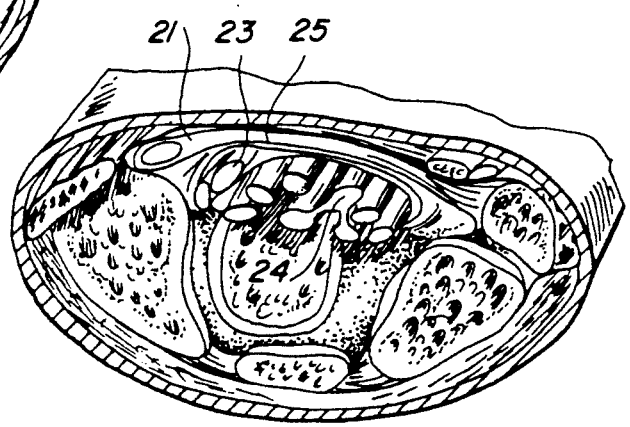
FIG. 4 illustrates a cross-section through the wrist of the hand illustrated in FIG. 3.

Extending the hand, as illustrated in FIG. 3, stretches flexor tendons 24 causing them to elongate and causes the thicker portions of the tendons from the forearm to enter the carpal canal, as illustrated in FIG. 4. The spreading of the palm and the entrance of the thicker portions of the tendons into the canal slightly enlarges carpal canal 25 and thus leads to relief of compression on median nerve 23.

Extending the thicker portions of the tendons into the carpal canal and stretching the transverse carpal ligament cause a transient aggravation of carpal tunnel syndrome since there is a transient increase of pressure within the carpal canal and thus on the median nerve. This may seem to be the opposite of an appropriate maneuver. However, because the carpal canal is also being enlarged, the end result of the treatment is a reduction in pressure on the median nerve and reduction or prevention of the symptoms of carpal tunnel syndrome.

Figure 5:
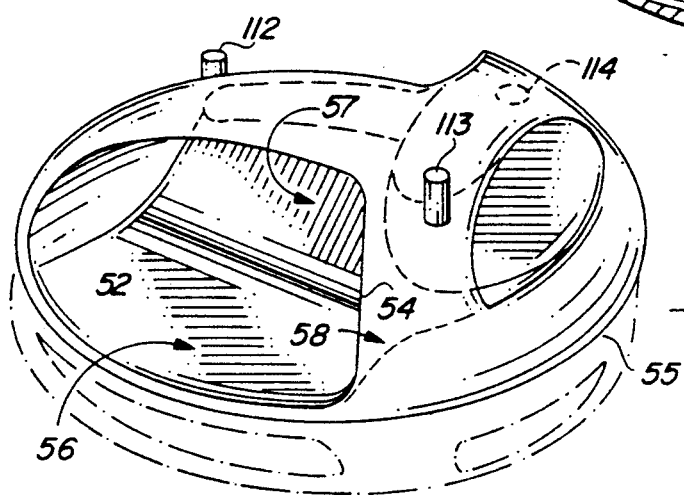
FIG. 5 is a perspective view of a glove constructed in accordance with the invention.

The manipulation of the hand as illustrated in FIG. 3 requires a resting place for the patient's fingers and the use of both hands of a physician. It is desired that a similar self-treatment be available from a glove that simulates manipulation and stretching by a physician. FIG. 5 illustrates a preferred embodiment of such a love. Glove 51 includes major surface 52 having a contoured shape, for extending the hand, and cover or strap 53, for holding the hand in position against the major surface. Glove 51 is intended for use with the left hand, which is inserted through opening 54. Right hand glove 55, illustrated in dashed line, is a mirror image of glove 51 and can be separate from or molded with glove 51 in a single piece of plastic.

Major surface 52 includes region 56 for the palm, region 57 for the fingers, and region 58 for the thumb. Region 56 is generally flat, with a recess described in more detail in conjunction with FIG. 7. Region 57 slopes upwardly away from region 56 for bending the fingers back relative to the palm. Region 58 slopes upwardly away from region 56 for bending the thumb back relative to the palm. Regions 56-58 blend smoothly into one another with no corners or abrupt changes in height.

Figure 6:
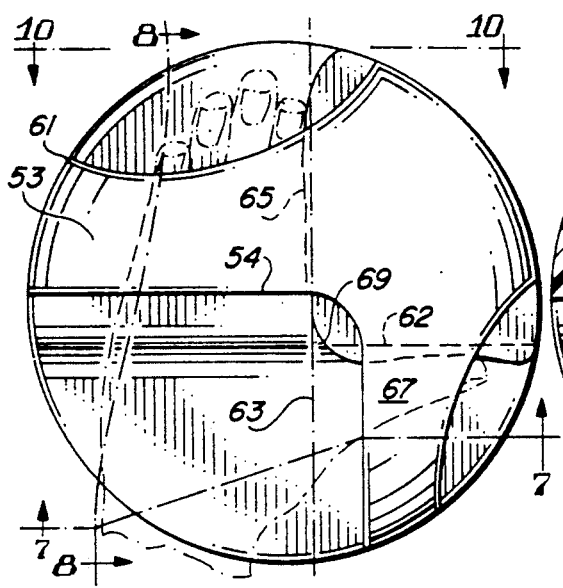
FIG. 6 is a top view of a glove constructed in accordance with the invention, showing the position for a left hand.

FIG. 6 illustrates a top view of the glove shown in FIG. 5. Plate 61 is divided into unequal quadrants by perpendicular lines 62 and 63. Line 62 is approximately aligned with the radial side of index finger 66 and line 63 is approximately under the knuckles. Wall 65 encloses a first quadrant, extending from the edge of plate 61 along index finger 66, around corner 69, then along thumb 67 back to the edge of plate 61. Rounded corner 69 fits the curve in the hand between the index finger and thumb. Wall 65 abducts thumb 67 and holds it approximately perpendicular to the index finger. The remaining fingers are held parallel to the index finger, in part by cover 53.

Figure 7:
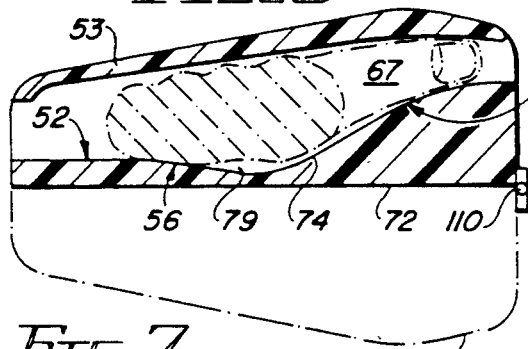
FIG. 7 is a cross-section along line 7—7, showing the extension of the thumb.

As illustrated in FIG. 7, the surface under thumb 67 increases in height with increasing distance from corner 69 or, more specifically, from line 62 (FIG. 6). This extends the thumb, thereby flattening the palm and stretching the transverse carpal ligament. The angle of the thumb is not critical, e.g. 25°-50° relative to bottom 72. Region 58, under the thumb, is joined to region 56, under the palm, by curved portion 74. Curved portion 74 is concave, i.e. it has a radius of curvature above the major surface of the glove. Region 58 preferably includes convex portion 77, having a radius of curvature below major surface 52. This provides a comfortable rest for the thumb and adapts the glove to hands of different sizes.

In region 56, diagonally opposite wall 65, recess 79 is near the edge of major surface 52, underneath the heel of the hand. Recess 79 in combination with region 58 opens the palm and stretches the transverse carpal ligament.

Figure 8:
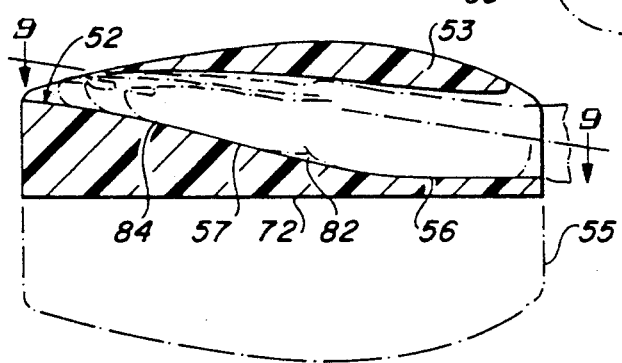
FIG. 8 is a cross-section along line 8—8, showing the extension of the fingers.

As shown in FIG. 8, region 56 under the palm is flat or slightly concave. Region 57, under the fingers, increases in height with increasing distance from corner 69 or, more specifically, from line 63 (FIG. 6) for stretching the flexor tendons. Regions 56 and 57 are joined by curved portion 82 having a radius of curvature above major surface 52. In a preferred embodiment of the invention, region 57 includes concave, curved portion 84, having a radius of curvature below major surface 52. This provides a comfortable rest for the fingers and adapts the glove to hands of different sizes. The slope of region 57 relative to bottom 72 is not critical, e.g. from 10° to 30° is suitable.

Figure 9:
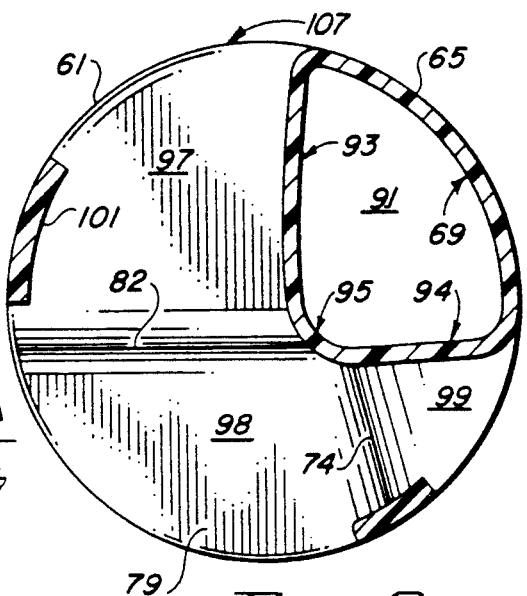
FIG. 9 is a cross-section through the glove of FIG. 6 in a plane parallel to surface of the drawing, showing the major surface of the glove.

FIG. 9 shows the major surface of the glove with cover 53 and wall 65 in cross-section. Wall 65 encloses quadrant 91 and includes first wall portion 93, for aligning the index finger, and second wall portion 94, for aligning the thumb at approximately 90° to the index finger. The first and second wall portions are connected by rounded corner 95. The interior of quadrant 91 can be hollow or filled and is preferably hollow. Exterior wall portion 96 could be omitted, but is kept to give the glove a more pleasing round or oval appearance.

Quadrant 97, opposite first wall portion 93, is bounded, in part, by section 101 of the cover. Section 101 confines the fingers and helps keep the fingers parallel to first wall portion 93. Quadrant 97 merges with quadrant 98 along curved portion 82. Quadrant 99, opposite second wall portion 94, merges with quadrant 98 along curved portion 74.

Figure 10:
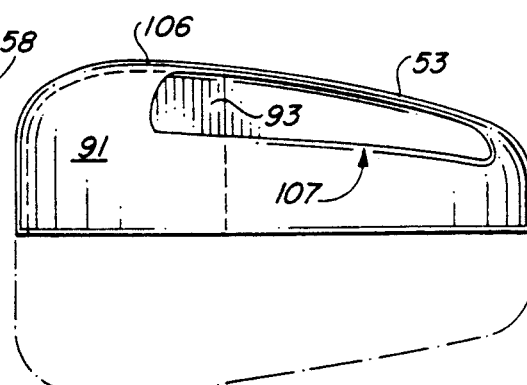
FIG. 10 is a side view of the glove of FIG. 6 along line 10—10.

In FIG. 10, portion 106 of cover 53 overlies quadrant 91 to provide a smooth outer surface merging with the edge of the plate. Similarly, the major surface merges with the edge of the plate at corner 107.

In use, the left hand is inserted into opening 54 (FIG. 6) with index finger 66 and thumb 67 aligned with wall 65. With glove 51 on a tabletop or other suitable surface, one leans on the hand with the elbow straight (extended) or slightly bent (flexed). Leaning into the glove bends the palm back relative to the forearm while the fingers are extended and the thumb is extended by the contours in the major surface of the glove. This use of the glove flattens the palm and directly stretches the transverse carpal ligament. It also extends the fingers and wrist which pulls the thicker portions of the flexor tendons through the canal, thereby indirectly further stretching the transverse carpal ligament and dilating (enlarging) the carpal canal. The stretching is continued for several seconds and then the hand is relaxed. Thus, proper use of glove 51 approximates the manipulation and stretching by a physician.

Having thus described the invention, it will be apparent to those of skill in the art that various modifications can be made within the scope of the invention. For example, left and right hand gloves can be molded separately and their bottom edges joined with adhesive. Alternatively, the gloves can be joined by hinge 110, as shown in FIG. 7, for opening the glove and treating both hands simultaneously. If left and right hand gloves are joined along their bottom edges, or molded as a single piece, pins 112 and 113 (FIG. 5) are added to each glove for defining a plane, with contact area 114, to support the glove on a horizontal surface. While the glove is shown in FIGS. 7 and 8 as constructed of solid plastic, the underside of the major surface can be hollow, provided that pressure on the major surface does not cause the plastic to distort. This lightens the glove and reduces the cost to manufacture. This does not mean that the major surface has to be rigid or hard. One could, for example, line the glove with cloth or other material for greater comfort. While cover 53 is preferably molded as an integral part of the glove, a separate strap could be attached at the edges of the plate instead. Wall 65 could be replaced with posts or other means to align the thumb and index finger. Wall 65 is preferred to posts since the wall positions the hand more accurately and is more comfortable. Although wall 65 is shown as perpendicular to the major surface, the wall could be sloped somewhat but not so much that the thumb or index finger slips during treatment.

What is claimed is:

1. An orthopedic appliance for the self-treatment or prevention of carpal tunnel syndrome by stretching the transverse carpal ligament and pulling the thicker portions of the flexor tendons through the carpal canal, said appliance comprising:

a plate having a first contoured major surface for receiving a hand and having a peripheral edge;

a wall intersecting said surface and including a first wall portion for positioning the index finger of the hand and a second wall portion for positioning the thumb of the hand, said first wall portion and said second wall portion being connected by a corner located on said first contoured major surface, said first wall portion and said second wall portion extending from said corner toward said peripheral edge;

said major surface increasing in height along said first and second wall portions with increasing distance from said corner, for extending the fingers and abducting and extending the thumb of the hand.

2. The appliance as set forth in claim 1 wherein said wall encloses a first quadrant of said plate and the palm of the hand rests on a second quadrant, diagonally opposite said first quadrant, and said major surface includes a recess in said second quadrant for stretching the transverse carpal ligament of the hand.

3. The appliance as set forth in claim 2 and further comprising a third quadrant opposite said first wall portion and a fourth quadrant opposite said second wall portion, wherein said major surface includes a first convex portion in said third quadrant and a second convex portion in said fourth quadrant.

4. The appliance as set forth in claim 3 and further comprising a first concave portion joining said second and third quadrants and a second concave portion joining said second and fourth quadrants.

5. The appliance as set forth in claim 1 and further comprising a strap for holding said appliance to the hand.

6. The appliance as set forth in claim 1 wherein said first major surface is contoured to receive a right hand and said appliance further includes a second major surface having a contour for receiving a left hand.

7. The appliance as set forth in claim 6 wherein said first and second major surfaces are opposite sides of said plate.

8. The appliance as set forth in claim 6 and further comprising a second plate wherein said first and second major surfaces are on respective ones of said first and second plates.

9. The appliance as set forth in claim 8 and further comprising a hinge interconnecting said first and second plates.

10. The appliance as set forth in claim 8 wherein said plates are joined together with said first and second major surfaces facing in opposite directions.

11. The appliance as set forth in claim 1 wherein said first and second wall portions meet at an angle of approximately ninety degrees.

12. A method for treating or preventing carpal tunnel syndrome by extending the wrist and hand relative to the forearm, said method comprising the steps of:

placing the hand on an appliance having a contoured major surface which extends the fingers and abducts and extends the thumb;

placing the appliance on a support;

extending the elbow adjoining the forearm;

leaning into the appliance with the elbow extended or slightly bent; and then relaxing the elbow and hand.

13. The method as set forth in claim 12 wherein the last two steps are repeated at least once.

* * * * *